(12) United States Patent
Kormann et al.

(10) Patent No.: US 6,251,366 B1
(45) Date of Patent: Jun. 26, 2001

(54) USE OF DISPERSIONS OF MAGNETO-IONIC PARTICLES AS MRI CONTRAST MEDIA

(75) Inventors: Claudius Kormann, Schifferstadt (DE); Michel Robert Anseau, Havré; Robert Nicolas Henry Muller, Mons, both of (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/396,340

(22) Filed: Feb. 28, 1995

Related U.S. Application Data

(63) Continuation of application No. 08/068,201, filed on May 27, 1993, now abandoned.

(30) Foreign Application Priority Data

Jun. 1, 1992 (EP) .................................................. 92109168

(51) Int. Cl.⁷ .................................................. A61B 5/055
(52) U.S. Cl. ...................................... 424/9.322; 424/9.32
(58) Field of Search ................................ 424/9.322, 900, 424/9.32; 564/492, 502, 836; 128/653.4, 654; 436/173

(56) References Cited

U.S. PATENT DOCUMENTS

| | | | |
|---|---|---|---|
| 4,675,173 | 6/1987 | Widder | 424/9 |
| 4,804,529 * | 2/1989 | Bardy et al. | 424/9 |
| 4,810,401 | 3/1989 | Mair et al. | 252/62.56 |
| 4,827,945 * | 5/1989 | Groman et al. | 128/653.4 |
| 4,985,233 * | 1/1991 | Klaveness et al. | 424/9 |
| 5,023,072 * | 6/1991 | Cheng | 424/9 |
| 5,043,101 * | 8/1991 | Gordon | 252/408.1 |
| 5,055,288 | 10/1991 | Lewis et al. | 424/9 |
| 5,143,716 * | 9/1992 | Unger | 424/9 |
| 5,160,725 * | 11/1992 | Pilgrimm | 424/9 |

FOREIGN PATENT DOCUMENTS

| | | |
|---|---|---|
| 252 254 | 1/1988 | (EP) . |
| 454 044 A2 | 10/1991 | (EP) . |
| WO 85/04330 | 10/1985 | (WO) . |
| 8911873 * | 12/1989 | (WO) . |

OTHER PUBLICATIONS

The effects of iron oxides on proton relaxivity, Josephson et al. Magnetic Resonance Imaging vol. 6, 647–653 (1988).

* cited by examiner

*Primary Examiner*—Diana Dudash
*Assistant Examiner*—Michael G. Hartley
(74) *Attorney, Agent, or Firm*—Keil & Weinkauf

(57) ABSTRACT

The invention relates to the use of dispersions of magneto-ionic particles consisting essentially of superparamagnetic solid particles and at least one polyelectrolyte as dispersing substance in water for the preparation of an MRI contrast medium.

2 Claims, No Drawings

USE OF DISPERSIONS OF MAGNETO-IONIC PARTICLES AS MRI CONTRAST MEDIA

This application is a continuation of application Ser. No. 08/068,201, filed on May 27, 1993 now abandoned.

The present invention relates to the use of dispersions of magneto-ionic particles consisting essentially of superparamagnetic solid particles and at least one polyelectrolyte as dispersing substance in water for the preparation of an MRI contrast medium.

The MRI technique (magnetic resonance imaging) permits the imaging of organs or regions of tissue. This entails the protons contained therein, especially those in the water, changing their magnetic behavior on exposure to a strong external magnetic field, and these changes and the differences in the proton concentration being determined and imaged. Since, however, the relative differences between the chemical and magnetic environment of the water molecules in the different organs and tissue portions are usually very small, the difference in intensity of the signals to be measured is also normally low so that corresponding images show little contrast. The contrast, which reflects the difference in intensity of two adjacent regions of the investigated object in the form of color levels, can be defined by formula 1

$$C=(I_a-I_b)/(I_a+I_b) \quad (1)$$

where C is the contrast and $I_a$ and $I_b$ are the intensity of two adjacent image or volume elements.

In order, nevertheless, to obtain the information which is necessary for a diagnosis using the MRI technique, which is an investigation method with few drawbacks compared with the use of X-rays or radioactive isotopes, it is known to employ contrast media which are adsorbed selectively on the various tissue portions or organ regions and, in this way, cause a measurable change in the magnetic states of the water molecules surrounding them. Contrast media of this type which are already in use contain either para-, superpara- or ferromagnetic substances. The mode of action of these contrast media is based on the generation of additional magnetic interactions between the proton and the static magnetic field. In this case the relaxation times $T_1$ and $T_2$ of the protons, and the relaxation rates $R_1$ [$s^{-1}$] and $R_2$ [$s^{-1}$], which correspond to the spin-lattice and the spin-spin coupling respectively, are measured and differ according to the chemical and physical environment of the organ or tissue protons (medium). It is thus possible for the measured relaxation rates to be stated as totals, according to formulae 2 and 3

$$R_1(\text{total})=R_1(\text{medium})+R_1(\text{contrast medium}) \quad (2)$$

and $$R_2(\text{total})=R_2(\text{medium})+R_2(\text{contrast medium}) \quad (3)$$

The relaxation rates $R_1$ and $R_2$ related to the effect per mole of ferrite in the contrast medium are called relaxivities $r_1$ and $r_2$ [$s^{-1}$ $M^{-1}$], and formulae 2 and 3 become formulae 2a and 3a.

$$R_1(\text{total})=R_1(\text{medium})+c \cdot r_1 \quad (2a)$$

and $$R_2(\text{total})=R_2(\text{medium})+c \cdot r_2 \quad (3a)$$

where c is the concentration of contrast medium in M. In order to minimize the amount of contrast medium necessary in diagnostic methods utilizing the MRI technique, it is evident from the formulae shown that the parameters $r_1$ and $r_2$ must be as large as possible.

The known MRI contrast media contain as magnetic materials those with either paramagnetic, superparamagnetic or ferromagnetic properties. Of these, the ferromagnetic media are generally impractical due to the large particle size of ferromagnetic particles. Many studies (eg. on the flow properties of water in capillaries) require non-settling extremely fine-grained magnetic contrast media. Thus the solid particle size should not be larger than 100 nm. The known paramagnetic contrast media are poor $T_2$ agents. It is the superparamagnetic contrast media which are of particular interest because, owing to their large effect both on $T_1$ and on $T_2$ of the magnetic nuclei, they have a marked effect on the image contrast (eg. U.S. Pat. Nos. 4,675,173, 5,055,288). These contrast media containing superparamagnetic colloids with a spin-spin and a spin-lattice relaxation which is higher than with ferromagnetic or paramagnetic colloids thus have higher $R^1$ and $R_2$ values and allow the concentration of the contrast medium to be lower in MRI investigations (Lee Josephson et al., Magnetic Resonance Imaging, Vol. 6, 647–653 (1988)).

Although they have enhanced $r_1$ and $r_2$ values the known superparamagnetic contrast media are still far from ideal because they have poorly balanced $r_2/r_1$ ratios. Prior art contrast media have, for example, values of $8 \times 10^3$ $M^{-1}s^{-1}$ for $r_1$ and of $4 \times 10^5$ $M^{-1}s^{-1}$ for $r_2$ (WO 85/04330) or of $4 \times 10^4$ $M^{-1}s^{-1}$ for $r_1$ and of $1.6 \times 10^5$ $M^{-1}s^{-1}$ for $r^2$ (U.S. Pat. No. 4,827,945).

A high $r_1$ value is required in order to keep the dose of the contrast medium to a minimum. In addition, a high $r_2/r_1$ ratio allows the contrast medium to be used for two purposes ie. as an effective positive and negative contrast medium.

The signal intensity I, is a complex function of the number of protons and of their relaxation rate. If $R_1$ is increased, I is increased too (positive action). If $R_2$ is increased I is decreased (negative action). Using conventional ultrafast imaging techniques it is possible to adjust the $T_2$ contribution (which is proportional to the $r_2$ parameter). Thus positive and negative intensity effects can be obtained provided $r_2$ is sufficiently high compared with $r_1$.

Thus there is no fine particle (particle diameter<100 nm) contrast medium reported that has $r_1 > 10^5$ $M^{-1}s^{-1}$ and that additionally maintains a value of $r_2/r_1$ greater than 7 (measured at 20 MHz, 37° C.). Therefore it is an object of the present invention to provide a formulation of superparamagnetic solid particles which is suitable for preparing dual purpose MRI contrast medium and which has, in particular, high relaxivities $r_1$ and $r_2$ and a high $r_2/r_1$ ratio.

We have found that this object is achieved by using dispersions of magneto-ionic particles consisting essentially of superparamagnetic solid particles and at least one polyelectrolyte with a molecular weight of from 1,000 to 25,000 as dispersing substance in water, where the superparamagnetic solid particles have a primary particle size of from 7 to 50 nm and a specific surface area of from 30 to 130 $m^2/g$ and are present in the dispersions of magneto-ionic particles in the form of colloidal units with on average only one superparamagnetic solid particle enveloped by the polyelectrolyte with a molecular weight of from 1,000 to 25,000 and with a charge number greater than 5 as dispersing substance, to prepare MRI contrast media with relaxivities $r_1$ greater than $9 \times 10^4$ $M^{-1}s^{-1}$ and a ratio of $r_2$ to $r_1$ of at least 7, measured at 20 MHz and 37° C. Thus $r_2$ will be greater than $6.3 \times 10^5$ $M^{-1}s^{-1}$. When measured at 10 kHz and 37° C., $r_1$ is greater than $5 \times 10^4$ $M^{-1}s^{-1}$ and when measured at 4 MHz and 37° C. it is greater than $1.5 \times 10^5$ $M^{-1}s^{-1}$.

The superparamagnetic solid particles contained in the dispersions of magneto-ionic particles used according to the invention are those which have a BET specific surface area of from 30 to 130 m²/g, preferably from 80 to 110 m²/g. The specific surface area was in this case determined by the DIN 66 132 method using a Ströhlein areameter supplied by Str öhlein, Düsseldorf, by the one-point difference method of Haul and Dümbgen. The median particle size is from 7 to 50 nm and in particular from 7 to 25 nm. Preferred classes of substances are superparamagnetic iron oxides such as $Fe_3O_4$, $\gamma$-$Fe_2O_3$, berthollides and, in particular, the cubic ferrites of the composition $M_vMn_wZn_xFe_yO_z$ described in U.S. Pat. No. 4,810,401.

These magnetic particles or mixtures containing these particles are coated with polyelectrolytes. The polyelectrolytes bring about not only a suitable steric stabilization but also an increase in the surface charge of the solid particles. Essential in this connection is the pH, which influences the stability of the suspension. It is possible, by altering the pH, to adjust in a suitable manner the charge carrier concentration in the polyelectrolytes and the volume of the absorbate layer. When anionic polyelectrolytes are used, it has proven expedient for the pH to be greater than their acid constant (pKa), whereas in the case of cationic polyelectrolytes the pH is preferably less than the pKa. A plurality of polyelectrolytes with a molecular weight of from 1,000 to 25,000 is suitable. These polymers preferably have from 5 to 1,000 charges in the molecular framework. Particularly suitable polyelectrolytes are from the group comprising polyacrylate, acrylic acid, acrylic acid/acrylamide copolymers, modified polyacrylates, phosphomethylated polycarboxylates, polvinylphosphonic acids, polyvinylphosphoric acids, polyamines, polyvinylamines, polysulfonic acids, polyphosphoric acids. In the case of the polyacrylates, a pH range of from 2 to 12 has proven particularly advantageous.

Another important parameter, besides the nature of the superparamagnetic particles and the polyelectrolytes, is the structure of the colloidal units which on average contain only one solid particle enveloped by the dispersing substance. This means that only one superparamagnetic primary particle is entrapped per superparamagnetic colloidal unit in the MRI contrast medium. The size of these primary particles can be determined by electron microscopy, X-ray line-broadening or BET measurements, while the size of the colloidal unit can be measured by light scattering. In a preferred embodiment, the colloidal units have a size of from 8 to 100 nm.

These dispersions of magneto-ionic particles which are suitable for use according to the invention can be prepared in a straightforward manner. This entails a mixture of water and the polyelectrolyte and/or its alkali metal salt in the form of a 10 to 90% by weight solution being stirred with the filter cake, which is normally still moist, of the superparamagnetic material, and the suspension subsequently being dispersed under the action of high shear forces for half an hour to 2 hours. The temperature may rise to 70° C. during this. The sequence of addition of the components is arbitrary and has no effect on the properties of the resulting magnetic liquid. Subsequently, centrifugation is carried out at from 200 to 2,000 g for from 10 minutes to 2 hours, and the small amount of sedimented particles is separated off.

These sedimentation-stable dispersions of magneto-ionic particles are then diluted to prepare the MRI contrast medium. This entails the colloidal units being separated from one another sufficiently far for them to have essentially no mutual influence within the scope of brownian motion of the molecules. An example of this is colloidal units with a diameter of about 100 nm, which contain a superparamagnetic primary particle of approximately 10 nm and which at a dilution of 100 mg per liter of water have a mutual distance of a few $\mu$m at room temperature.

The dispersions of magneto-ionic particles with this characteristic result, when used for MRI contrast media, in reagents with relaxivities $r_1$ greater than $9 \times 10^4$ $M^{-1}s^{-1}$ and $r_2$ greater than $6.3 \times 10^5$ $M^{-1}s^{-1}$ and $r_2$:$r_1$ ratios of at least 7, measured at 20 MHz and 37° C.

The examples illustrate the invention.

EXAMPLE 1

813 g of $FeCl_3 \times 6$ $H_2O$, 282 g of $FeCl_2 \times 4$ $H_2O$ and 105 g of $MnCl_2 \times 4$ $H_2O$ in 1650 g of water are added under nitrogen to a solution of 545 g of NaOH, 29 g of ZnO and 545 g of water within 60 min at 30° C. The pH at the end of the precipitation is 13.3. Dilute HCl is added until pH 11 is reached. The suspension is kept at 70° C. for 1 hour. After cooling to room temperature the pH is adjusted to 9 using dilute HCl. The suspension is filtered and washed. The resulting magnetic powder is characterized after drying at 80° C. as follows: specific BET surface area: 101 m²/g, saturation magnetization: 76 nTm³/g.

360 g of aqueous suspension are prepared by adding water to 123 g of magnetic pigment (from the filter cake of the above filtration and washing procedure). To this aqueous suspension a solution of 24.7 g of the sodium salt of polyacrylic acid (molecular weight ca. 4000) and 30 g of water is added. The dispersion is treated with an Ultra Turrax disperser for 1 hour at 10000 rpm. Then the suspension is centrifuged for 1 hour at 1000 g. The sedimentation after a 10 cm column has stood for 1 week is found to be less than 2%. The final stock suspension is prepared 5 weeks later by adding 18 g of the sodium salt of the above polyacrylic acid and 20 g of water to 237 g of the above centrifuged ferrite suspension and diluting to a final concentration of 100 mg of ferrite per liter.

Measurements of $T_2$ were performed with an M.R. relaxometer (Minispec PC/20, Series, Bruker, Germany) operating at a field strength of 0.47 T.

The $T_2$ relaxation times were calculated from data points generated with a C.P.M.G. multi-echo sequence. Measurements of $T_1$ were determined by calculation from data points generated by a standard inversion recovery pulse sequence. In addition field cycling relaxometry between 0.01 MHz and 50 MHz was carried out for the determination of the relaxivities $r_1$ as function of the magnetic field strength.

Stable aqueous suspensions were diluted to 5, 10, 20, 30 mg of ferrite/L. The stability of the suspension has been found to be excellent for more than one year by repeating the measurements (using the 100 mg/L stock solution).

Measurements of the suspensions show exceptional values for $r_1$ and $r_2$ indicative of a very high number of colloidal units and of the absence of agglomerates in well dispersed liquids. $r_1$ is consistently of the order of $1.2 \times 10^5$ $M^{-1}s^{-1}$ and $r_2$ is $1 \times 10^6$ $M^{-1}s^{-1}$ at 20 MHz. At lower fields longitudinal relaxivities $r_1$ are higher, i.e. $3.5 \times 10^5$ $M^{-1}s^{-1}$ at 2 MHz.

Provoked irreversible agglomeration shows a dramatic effect on the relaxivities. As an example the introduction of $Ca^{++}$ in a suspension of 9.7 mg/L can provoke the formation of a number of agglomerates of about 1 $\mu$m diameter (as measured by light scattering techniques) after twenty minutes. As a consequence relaxivities $r_2$ drop from about $10^6$ $M^{-1}s^{-1}$ to $10^5$ $M^{-1}s^{-1}$ (measured at 20 MHz and 37° C.).

EXAMPLE 2

542 g of $FeCl_3 \times 6$ $H_2O$, 188 g of $FeCl_2 \times 4$ $H_2O$, 32 g of $ZnCl_2$, 70 g of $MnCl_2 \times 4$ $H_2O$ and 10 ml of conc. HCl in 1100 ml of water are added under nitrogen to 369 g of NaOH in 380 g of water within 27 min at 30° C. The pH at the end of the precipitation is 11. The suspension is kept at 80° C. for 1 hour. Finally the pH is adjusted to 5 using dilute HCl. The suspension is filtered and washed. The resulting magnetite power is characterized after drying at 80° C. as follows: specific BET surface area: 94 m$^2$/g, saturation magnetization: 88 nTm$^3$/g. An elemental analysis of the dried magnetic powder yields the following weight contents: Mn: 3.3%, Zn: 4.8%, Fe: 57.5%.

A mixture of 12.3 g of the sodium salt of polyacrylic acid (molecular weight ca. 4000) and 15 g of water is added to the wet filter residue (containing 25 g of ferrite and 174 g of water). The dispersion is treated with an Ultra Turrax disperser for 30 min at 10000 rpm. After standing for 1 week the supernatant suspension (ca. 90%) is diluted to 100 mg/L of ferrite and is used as stock suspension for further measurements.

The measurements of $r_1$ and $r_2$ yield almost the same results as in Example 1, $r_1$ is $1.4 \times 10^5$ M$^{-1}$s$^{-1}$ and $r^2$ is $1 \times 10^6$ M$^{-1}$s$^{-1}$.

EXAMPLE 3

A well dispersed suspension of magnetite with a saturation magnetization $M_s$ of 61 nTm$^3$/g and a BET surface area of 84 m$^2$/g was prepared according to the following procedure:

542 g of FeCl$_3 \times$6 H$_2$O and 315 g of FeCl$_2 \times$4 H$_2$O in 1100 ml of water are added under nitrogen to 364 g of NaOH in 1100 ml of water within 17 min at 30° C. The pH at the end of the precipitation is 9.7. The suspension is kept at 70° C. for 1 hour. Finally the pH is adjusted to 9 using dilute HCl. The suspension is filtered and washed. The resulting magnetite powder is characterized after drying at 80° C. as follows: specific BET surface area: 84 m$^2$/g, saturation magnetization: 61 nTm$^3$/g.

A mixture of 13.9 g of the sodium salt of polyacrylic acid (molecular weight ca. 4000) and 17 g of water is added to the filter residue (containing 28 g of magnetite and 214 g of water). The dispersion is treated with an Ultra Turrax disperser and 30 min at 10000 rpm. After standing for 1 week the supernatant suspension (ca. 90%) is diluted to 100 mg/L of ferrite and is used as stock suspension for further measurements.

As in Example 1 diluted suspensions of 5, 10, 20, 30 mg of magnetite/L have been prepared from aqueous suspensions of 100 mg/L.

Suspensions prepared from the original batch at six-month intervals show excellent unchanged stability as confirmed by NMR measurements. Measurements of $T_1$ and $T_2$ carried out with the same procedure as in Example 1 show exceptional values for $r_1$ and $r_2$ also indicative of a very high number of colloidal units and of the absence of agglomerates. $r_1$ is consistently of the order of $10^5$ M$^{-1}$s$^{-1}$ and $r_2$ is $10^6$ M$^{-1}$s$^{-1}$ at 20 MHz and 37° C.

EXAMPLE 4

87 g of FeCl$_3 \times$6 H$_2$O, 32 g of FeCl$_2 \times$4 H$_2$O and 19 g MnCl$_2 \times$4 H$_2$O in 170 ml of water are added under nitrogen to a solution of 56 g of NaOH and 5 g of ZnO in 190 g of water within 12 min at 25° C. The pH at the end of the precipitation is 11.5. The suspension is kept at 80° C. for 1 hour. Finally, after cooling to room temperature, the pH is adjusted to 9 using dilute HCl. The suspension is filtered and washed. The resulting magnetic powder is characterized after drying at 80° C. as follows: specific BET surface area: 119 m$^2$/g, saturation magnetization: 77 nTm$^3$/g. An elemental analysis of the dried magnetic powder yields the following weight contents: Mn: 6.5%, Zn: 7.8%, Fe: 54.3%.

A mixture of 14 g of the sodium salt of polyacrylic acid (molecular weight ca. 4000 and 17 g of water is added to the filter residue (28 g of ferrite and 187 g of water). The dispersion is treated with an Ultra Turrax disperser for 30 min at 10000 rpm. After 1 week of rest the supernatant suspension (ca. 90%) is diluted to 100 mg/L and is used as stock suspension for further measurements.

As in Example 1 aqueous suspensions are diluted to 5, 10, 20, 30 mg/L.

Measurements of $T_1$ and $T_2$ are carried out with the same procedures as in Example 1, and $r_1$ is found to be $1.2 \times 10^5$ M$^{-1}$s$^{-1}$ and $r_2$ is $1.1 \times 10^6$ M$^{-1}$s$^{-1}$.

EXAMPLE 5

79 g of FeCl$_3 \times$6 H$_2$O, 29 g of FeCl$_2 \times$4 H$_2$O and 16 g MnCl$_2 \times$4 H$_2$O in 160 ml of water are added under nitrogen to a solution of 53 g of NaOH and 6.5 g of ZnO in 190 g of water within 16 min at 25° C. The pH at the end of the precipitation is 12. The suspension is kept at 80° C. for 1 hour. After cooling to room temperature the pH is found to be 9.2. The suspension is filtered and washed. The resulting magnetic powder is characterized after drying at 80° C. as follows: specific BET surface area: 112 m$^2$/g, saturation magnetization: 62 nTm$^3$/g. An elemental analysis of the dried magnetic powder yields the following weight contents: Mn: 8.4%, Zn: 10.3%, Fe: 47.4%.

A mixture of 12 g of the sodium salt of polyacrylic acid (molecular weight ca. 4000 and 15 g of water is added to the filter residue (25 g of ferrite and 169 g of water). The dispersion is treated with an Ultra Turrax disperser for 30 min at 10000 rpm. After 1 week of rest the supernatant suspension (ca. 90%) is diluted to 100 mg/L of ferrite and is used as stock suspension for further measurements.

As in Example 1 aqueous suspensions are diluted to 5, 10, 20, 30 mg/L. Measurements of $T_1$ and $T_2$ are carried out with the same procedure as in Example 1. The same relaxivities as in example 1 are obtained.

We claim:

1. A dual purpose MRI contrast medium consisting essentially of an aqueous dispersion of superparamagnetic solid particles and at least one polyelectrolyte which acts as a dispersant, said polyelectrolyte having an average molecular weight of from 1,000 to 25,000 said superparamagnetic solid particles having a primary particle size of from 7 to 50 nm and a specific surface area of from 30 to 130 m$^2$/g and being present in the dispersions in the form of colloidal units with on average only one superparamagnetic solid particle enveloped by the polyelectrolyte, and said polyelectrolyte having a charge number greater than 5, with the proviso that the relaxivities of the contrast media are such that $r_1$ is greater than $9 \times 10^4$ M$^{-1}$s$^{-1}$ and the ratio of $r_2$ to $r_1$ is at least 7, measured at 20 MHz and 37° C.

2. A dual purpose MRI contrast medium comprising a dispersion as claimed in claim 1, wherein $r_1$ is greater than $5 \times 10^4$ M$^{-1}$s$^{-1}$, measured at 10 kHz and 37° C. and is greater than $1.5 \times 10^5$ M$^{-1}$s$^{-1}$ when measured at 4 MHz and 37° C.

* * * * *